United States Patent [19]

Wegener et al.

[11] 4,405,527

[45] Sep. 20, 1983

[54] PROCESS FOR THE PREPARATION OF POLYISOCYANATES

[75] Inventors: Gerhard Wegener, Wuppertal; Hartmut Knöfel, Odenthal; Günther Ellendt; Marcel Petinaux, both of Krefeld, all of Fed. Rep. of Germany

[73] Assignee: Bayer Aktiengesellschaft, Leverkusen, Fed. Rep. of Germany

[21] Appl. No.: 397,652

[22] Filed: Jul. 12, 1982

[30] Foreign Application Priority Data

Jul. 24, 1981 [DE] Fed. Rep. of Germany ....... 3129270

[51] Int. Cl.$^3$ ............................................. C07C 118/02
[52] U.S. Cl. ............................................. 260/453 PH
[58] Field of Search ................................. 260/453 PH

[56] References Cited

U.S. PATENT DOCUMENTS 3,835,172 9/1974 Arndt et al. .................. 260/453 PH

OTHER PUBLICATIONS

Ullmans Encyklopadie der Technischen Chemie, 4th Edition (1977), vol. 13, pp. 350 et seq.

Primary Examiner—Dolph H. Torrence
Attorney, Agent, or Firm—Gene Harsh; Joseph C. Gil; Lyndanne M. Whalen

[57] ABSTRACT

Polyisocyanates are prepared by reacting a polyamine solution with a phosgene solution. Excess phosgene and hydrogen chloride formed during the reaction are removed from the reaction mixture. The solvent is subsequently removed from the reaction mixture (e.g., by evaporation and condensation) and treated with a compound containing isocyanate reactive hydrogen atoms to convert any isocyanates present into urethanes and/or ureas. The thus-treated solvent may then be reused, preferably after any urethanes and/or ureas present in the solvent have been removed.

7 Claims, No Drawings

PROCESS FOR THE PREPARATION OF POLYISOCYANATES

BACKGROUND OF THE INVENTION

The present invention relates to a process for the preparation of organic polyisocyanates in the presence of solvents. More particularly, it relates to a process in which the solvent put into the process is reused after at least part of the solvent is treated with compounds containing isocyanate reactive hydrogen atoms.

Organic polyisocyanates are produced on an industrial scale by phosgenation of the corresponding primary polyamines in the presence of inert organic solvents such as chlorobenzene or ortho-dichlorobenzene (see, e.g., Ullmans Encyklopä die der technischen Chemie, 4th Edition (1977), Volume 13, page 350 et seq). In the production of polyisocyanates (particularly, hexamethylene diisocyanate, tolylene diisocyanates and polyisocyanates of the diphenyl methane series) by such a process traces of compounds containing isocyanate groups are invariably formed (e.g., 6-chlorohexyl isocyanate in the production of hexamethylene diisocyanate; tolyl isocyanate in the production of tolylene diisocyanates; and phenyl isocyanate in the production of polyisocyanates of the diphenyl methane series by the phosgenation of aniline/formaldehyde condensates). Such isocyanate group-containing compounds have an extremely deleterious effect on the quality of the end products. The amount of such deleterious isocyanates in the product polyisocyanates has been reduced by removing the deleterious isocyanates from the product polyisocyanate. The solvent which is distilled off with the unwanted isocyanates is subsequently treated in an elaborate column distillation to remove any impurities before the solvent is reused. This purification of the solvent by distillation is possible only with a considerable expenditure of energy and outlay in apparatus. Further, those undesirable compounds having a boiling point near the boiling point of the solvent used are extremely difficult or impossible to remove.

SUMMARY OF THE INVENTION

It is an object of the present invention to provide a process for the production of polyisocyanates in which virtually no unwanted monoisocyanates are present.

It is also an object of the present invention to provide a process for the production of polyisocyanates from solutions of amines and phosgene in which the solvent is recovered and may be reused.

It is another object of the present invention to provide a process for the production of polyisocyanates from amine solutions and phosgene solutions in which the solvent is recovered in a simple and economical manner and may be reused.

It is yet another object of the present invention to provide a process for the production of polyisocyanates in which virtually all by-products are removed from recovered solvent before that solvent is reused.

These and other objects which will become apparent to those skilled in the art are accomplished by reacting a polyamine solution with a phosgene solution, removing excess phosgene and any hydrogen chloride present, removing the solvent from the reaction mixture and treating the solvent with a compound containing isocyanate reactive hydrogen atoms. The treated solvent may then be reused, preferably after any urethanes and/or ureas present in the solvent have been removed.

DETAILED DESCRIPTION OF THE INVENTION

The present invention is a process for the preparation of polyisocyanates in which (i) solutions of the polyamines on which the product polyisocyanates are based in an inert solvent are reacted with (ii) a solution of phosgene in an inert solvent by a single stage or multistage phosgenation reaction. The excess phosgene and the hydrogen chloride formed from the liquid reaction mixture are then removed. Subsequently, the solvent together with readily volatile compounds containing isocyanate groups are separated from the reaction mixture (e.g., by evaporation) and the product polyisocyanate is recovered as evaporation residue. The product polyisocyanate may be further purified by distillation. Volatile solvent-containing compounds having isocyanate groups are recovered by condensation of the vapors from the separation. Part of the condensate may be used for the preparation of amine solution (i) and part of the condensate may be used for the preparation of phosgene solution (ii). Either the total quantity of condensate thus-obtained or the portion containing compounds having isocyanate groups present which is to be reused in making amine solution (i) is treated with compounds containing isocyanate reactive hydrogen atoms. Any difficultly volatile reaction products formed by the reaction of these compounds containing isocyanate reactive hydrogen groups with isocyanate group-containing compounds present in the condensate may then be removed from the solvent by distillation.

The phosgenation reaction may be carried out in accordance with techniques known to those in the art using solutions of polyamines in inert solvents and phosgene solutions in inert solvents. Phosgenation may be carried out in one or more stages in the process of the present invention by, for example, the formation of suspensions of carbamic acid chlorides at low temperatures followed by conversion of the resulting suspensions into polyisocyanate solutions at higher temperatures ("cold/hot phosgenation"). Particularly suitable amines for the phosgenation reaction of the present invention are the technically important polyamines such as hexamethylene diamine; 2,4- and/or 2,6-diaminotoluene; 2,4'- and 4,4'-diaminodiphenyl methane and their mixtures with higher homologues (referred to as "polyamine mixtures of the diphenyl methane series") such as may be obtained in known manner by aniline/formaldehyde condensation; 1,5-diaminonaphthalene; 1-amino-3,3,5-trimethyl-5-aminomethyl-cyclohexane (isophorone diamine); tris-(isocyanatophenyl)-methane; or perhydrogenated diaminodiphenyl methanes.

In the process of the present invention, the above-described amines are generally used in the form of 3 to 40 wt. %, preferably 5 to 25 wt. % solutions in inert solvents.

The phosgene for the phosgenation reaction is generally used in the form of 10 to 60 wt. %, preferably 25 to 50 wt. % solutions in inert solvents.

Suitable inert solvents both for the polyamine and for the phosgene are, for example, chlorobenzene or ortho-dichlorobenzene.

After phosgenation, excess phosgene and the hydrogen chloride formed are removed in accordance with techniques known to those in the art. Such methods include blowing out the phosgene and hydrogen chloride with inert gas or partial distillation. The phosgenation product present after this removal is in the form of a solution and may be separated (e.g., by simple evaporation) into a gaseous phase containing volatile compounds having isocyanate groups and a liquid phase which is substantially completely crude polyisocyanate. The liquid phase thus-obtained may, if desired, be worked up by distillation in known manner to obtain the product polyisocyanate in a purer state. The separation of the phosgenation product into a volatile compound-containing phase and the product polyisocyanate is generally carried out at a temperature of from 80° to 220° C., preferably from 120° to 190° C. and at a pressure of from 100 to 4,000 mbar, preferably from 200 to 3,000 mbar. The vapors containing compounds having isocyanate groups are condensed to form a solvent condensate of the solvent-containing volatile isocyanates, in particular, monoisocyanates. The proportion of the volatile isocyanates (calculated as NCO with molecular weight 42) present in the condensate is generally from 50 to 5,000 ppm, preferably from 100 to 1,500 ppm.

In contrast to the processes known in the art, the elaborate column distillation typically employed for removing the compounds containing isocyanate groups is replaced in the present invention by one of the treatments described below before the solvent is reused.

In one embodiment of the present invention, the condensate containing volatile isocyanates is treated with a compound containing isocyanate reactive hydrogen atoms before separation into partial streams intended for the preparation of amine solution (i) and phosgene solution (ii). Difficultly volatile reaction products formed by the reaction of these compounds containing isocyanate reactive hydrogen atoms with the compounds containing isocyanate groups are removed by distillation of the solvent. The reaction and isolation of the pure solvent by distillation may be carried out in either one or several stages.

Whereas, separation of the readily volatile compounds containing isocyanate groups requires an elaborate fractional distillation, the difficultly volatile reaction products may easily be collected in the sump of the distillation apparatus and then removed.

The compounds containing isocyanate reactive hydrogen atoms which may be used in the practice of the present invention are generally compounds which do not form an azeotropic mixture with the solvent and which have a sufficiently higher boiling point than the solvent to allow separation by distillation. Suitable isocyanate reactive compounds include monohydric and higher hydric alcohols, preferably containing primary hydroxyl groups; monofunctional and polyfunctional primary and secondary amines and mixtures of such compounds. It is preferred to use compounds containing at least two isocyanate reactive compounds. These compounds may also be used in the form of solutions in a solvent of the type to be treated. Typical examples of such isocyanate reactive compounds are: (1,3)-butanediol; (1,4)-butanediol; (1,6)-hexanediol; 2,2,5-trimethyl-(1,6)-hexanediol; diethyleneglycol; triethyleneglycol; tetraethyleneglycol; glycerol; trimethylol propane; n-octadecanol; aniline; 2,2'-, 2,4'- and 4,4'-diaminodiphenyl methane and mixtures of these isomers with higher homologs (such as are obtained in known manner by aniline/formaldehyde condensation); 2,4- and/or 2,6-diaminotoluene; 1-aminonaphthalene; 1,5-diaminonaphthalene; tetramethylene diamine; hexamethylene diamine; isophorone diamine; and 4,4'-diaminodicyclohexyl methane.

Treatment of the condensate with the above-described compounds containing isocyanate reactive hydrogen atoms is generally carried out within the temperature range of from 80° to 200° C., preferably from 100° to 160° C. and, most preferably, from 120° to 155° C. To achieve close to quantitative removal of the compounds containing isocyanate groups, the compounds containing isocyanate reactive hydrogen atoms should be used in at least equivalent quantities (based on the isocyanate groups of the compounds in the condensate). Since the compounds containing isocyanate reactive hydrogen atoms are preferably compounds having a high boiling point, they can readily be separated from the solvent by distillation and may, therefore, be used in excess. The use of a subequivalent quantity isocyanate reactive compound would, of course, result in only partial removal of the compounds containing isocyanate groups. The equivalent ratio of isocyanate groups present in the compounds which are to be removed from the solvent to the isocyanate reactive groups (hydroxyl and/or amino groups) should generally be from 1:1 to 1:2.

It is in principle possible to use compounds containing isocyanate reactive hydrogen atoms which have a lower boiling point than the solvent to be recovered. Such lower boiling isocyanate reactive compounds (e.g., methanol, ethanol, ethylamine or n-hexylamine) react with the compounds containing isocyanate groups to form reaction products which have a higher boiling point than the solvent which is to be worked up. However, because these compounds containing isocyanate reactive hydrogen atoms have a lower boiling point than the solvent to be recovered and, therefore, are not obtained in the distillation sump, they should only be used in subequivalent quantities or at most, equivalent quantities. The compounds containing isocyanate groups would, however, only be partially removed when such quantities are employed.

The treatment of the solvent condensate with compounds containing isocyanate reactive hydrogen atoms may be carried out either at the stage of distillation itself or at a reaction stage preceding the distillation stage. If treatment is carried out within the temperature range of 80° to 200° C., it is generally completed after an average dwell time of from 5 to 60 minutes. The primary amines require a shorter dwell time than the alcohols due to their greater reactivity with isocyanate groups.

In this embodiment of the process of the present invention, the difficultly volatile reaction products formed are generally discharged from the distillation sump in the form of concentrates. These concentrates are from 5 to 95 wt. %, preferably from 20 to 85 wt. % and, most preferably from 35 to 60 wt. % difficultly volatile reaction product.

The solvent obtained as distillate freed from compounds carrying isocyanate groups may then be reused for the preparation of amine solution (i) and phosgene solution (ii). Polyisocyanates containing a greatly reduced proportion of readily volatile isocyanate components are thus-obtained at reduced cost in energy and outlay in apparatus.

The process of the present invention has the further advantage that the amines used as starting materials in the phosgenation reaction may contain a higher proportion of by-products, which would result in formation of a correspondingly higher proportion of isocyanate group-containing compounds to be removed than could be tolerated in known processes. As a result, the cost in energy and outlay in apparatus required for the preliminary preparation of the amine starting material is considerably reduced in the process of the present invention. Thus, condensation products of aniline and formaldehyde (MDA), for example, could be used in the process of the present invention after simple distillation in a water jet vacuum. The aniline content of the thus-treated condensation products was 10 to 20 times as high as that of products which had additionally been subjected to steam distillation.

In another embodiment of the present invention, the solvent condensate containing volatile compounds having isocyanate groups is sub-divided into two streams corresponding to the size of the streams of amine solution (i) and phosgene solution (ii). Each of these streams may be reused as solvent for the preparation of these solutions but the stream used in preparing the amine solution (i) must first be treated with an isocyanate reactive compound. In both embodiments of the process of the present invention, the proportion by weight of the solvent stream for the preparation of the amine solution to the solvent stream for the preparation of the phosgene solution is in the range of from 10:1 to 1:5.

In the second embodiment of the present invention, that partial stream of the solvent condensate which is used for the preparation of phosgene solution (ii) may be used without being treated further. Only that partial stream which is used for the preparation of amine solution (i) need be subjected to treatment with an isocyanate reactive compound. Working up by distillation of the partial stream which is treated may, however, be dispensed with. Due to the continuous conversion of a portion of the isocyanate group-containing compounds in the continuously circulating solvent into secondary products which are free from isocyanate groups, the total quantity of isocyanate compounds present in the system does not exceed a tolerable maximum. The reaction products containing urethane groups and, in particular, urea groups (resulting from the reaction of the isocyanate compounds with the compounds containing isocyanate reactive hydrogen atoms), remain in the end product if the treated solvent is not distilled. When the end product is distilled, however, these reaction products containing urethane groups or urea groups may be removed as residues. These by-products are physiologically harmless substances (in contrast to the volatile monoisocyanates) and are present in extremely small concentrations so that they have no significant influence on the quality of the end product.

The compounds with isocyanate reactive hydrogen atoms used in the second embodiment of the process according to the invention are preferably the primary amines exemplified above. The polyamines used as the starting material for the production of the polyisocyanate are particularly preferred.

In one variation of the second embodiment of the invention described above, the partial stream of solvent used for the preparation of amine solution (i) is treated with an isocyanate reactive compound in a special reactor provided for the purpose. Subsequent distillation of the treated partial stream before it is used as amine solvent removes the difficultly volatile reaction products of the compounds containing isocyanate groups with compounds containing OH groups or amine groups.

In another variation of the second embodiment of the invention, the partial solvent stream used for the preparation of amine solution (i) is treated with compounds containing isocyanate reactive hydrogen atoms in a reactor specially provided for this purpose. In this variation, the compounds containing isocyanate reactive hydrogen atoms are preferably primary amines of the type exemplified above. Primary aliphatic amines are particularly preferred because of their high reactivity with isocyanate groups. The compounds containing isocyanate reactive hydrogen atoms are preferably used in an equivalent ratio of from 0.9:1 to 1.2:1 of primary amino groups to isocyanate groups present in the isocyanate component to be separated. If the polyamine used to treat the condensate is the same as that used as the starting material for the production of the polyisocyanates, large excesses of the polyamine may, of course, be used. The treatment of the condensate with an isocyanate reactive compound may be carried out at a temperature within the range of 80° to 200° C. and at an average dwell time of the reaction components in the compounds with which they are reacted of from 5 to 60 minutes. The partial solvent stream treated as described above may then be used for the preparation of amine solution (i) without further purification by distillation.

In another variation of the process of the present invention, the polyamine used as the starting material for the preparation of the polyisocyanates is also used for treating the partial solvent stream used for the preparation of amine solution (i). The partial solvent stream to be used for the preparation of amine solution (i) is transferred without further preliminary treatment into a reactor used for the preparation of amine solution (i). Because of the extremely high excess of amino groups present, the isocyanate groups present in the compounds contained in the condensate are converted virtually quantitatively into urea groups. This third variation of the process of the present invention is based on the surprising observation that even without elaborate column distillation to remove the readily volatile compounds containing isocyanate groups, a marked reduction in the amount of such unwanted compounds present in the end product of the process (polyisocyanate) can be achieved if the condensate is used for the preparation of the starting solutions.

The advantage of the second embodiment of the invention described above lies in the fact that less effort is required for distillation to purify the solvent than in the first embodiment because the quantity of partial stream treated is less than in the first embodiment or because distillation is eliminated.

Having thus described the invention, the following examples illustrate the process of the present invention.

EXAMPLES

Example 1

(1a) Chlorobenzene containing 2,000 ppm of phenyl isocyanate was continuously fed to a reactor at a rate of 2,500 grams/hour. This solution was reacted with an 18% by weight solution of tetraethylene glycol in chlorobenzene fed into the reactor at a rate of 25 gm/hour (corresponding to a 10% excess of OH equivalents, based on the isocyanate equivalents). The reaction was carried out at a temperature of 130° C. in a reactor consisting of a series of three stirrer vessels for an average dwell time of 30 minutes. The reaction mixture was thereafter continuously fed into the sump of a distillation column. The chlorobenzene used to make the above-described phenyl isocyanate solution was obtained by removing phosgene and hydrogen chloride and then evaporating the solvent from the product of a commercial phosgenation of aniline/formaldehyde condensates followed by condensation of the evaporated solvent. Before the reaction mixture was fed into the sump of the column, 1,900 g of monochlorobenzene together with 100 g (0.84 mol) of phenyl isocyanate and 89.6 g (0.92 mol OH) of tetraethylene glycol were introduced into the sump and circulated by pumping for 2 hours at 130° C. without distillation.

As the reaction mixture began to be fed into the sump, a quantity of distillate corresponding to the quantity of monochlorobenzene introduced from the reactor was continuously removed from the head of the column at a slightly raised sump temperature without reflux (at normal pressure).

The phenyl isocyanate content in the chlorobenzene under these conditions (operating time 10 hours) was 30 ppm.

(1b) By doubling the volume of the preliminary reactor without changing the reaction conditions and flow rates of the streams, the dwell time in the preliminary reaction stage was increased to 60 minutes. The proportion of phenyl isocyanate in the chlorobenzene under these conditions (operating time 10 hours) was less than 10 ppm.

(1c) After introduction of the reaction mixture into the sump was terminated, the sump of the distillation column was concentrated by evaporation to a residual monochlorobenzene content of 15 wt. %. The phenyl isocyanate content in the distillate obtained in this case was also less than 10 ppm.

The presence of tetraethylene glycol (i.e., OH groups) could not be detected in the distillates of (1a), (1b) and (1c) under the given experimental conditions.

(1d) The sump product from (1c) was heated to 200° C., most of the residual monochlorobenzene being removed by distillation. The product was then heated to 240° C. under a vacuum of 30 Torr and a total of 74 g (0.62 M) of phenyl isocyanate was collected. The sump product again contained reactive OH groups and was recycled. It was determined that loss of OH equivalents occurring due to side reactions under the experimental conditions could be compensated for by discharging 10 wt. % of the sump product of (1d) after each cycle and adding a corresponding quantity of tetraethylene glycol before reuse.

Example 2

Example 1 was repeated using the same apparatus and the same conditions, except that monochlorobenzene also containing 2,000 ppm of phenyl isocyanate was fed into the reactor at a rate of 2,500 grams/hour and distilled without the addition of tetraethylene glycol and without the introduction of phenyl isocyanate into the sump of the column. The phenyl isocyanate content in the distillate was 800 ppm and increased during the course of the experiment (operating time 10 hours) to about 900 ppm.

Example 3

Example 1 was repeated using an isocyanate-containing monochlorobenzene obtained from MDI solvent phosgenation and having an isocyanate content of 700 ppm (based on molecular weight of NCO=42) as a starting material. The impurities present in this starting material which contained isocyanate groups consisted of about 80 wt. % phenyl isocyanate and the remainder, higher boiling components such as isocyanatobenzyl chloride and MDI isomers.

After a dwell time of 60 minutes in the preliminary reactor and treatment in the same manner described in Examples 1 and 2, the proportion of isocyanate components in the distillate was less than 10 ppm of isocyanate (based on NCO with molecular weight 42).

Example 4

A monochlorobenzene solution having a phenyl isocyanate content of 500 ppm was fed into a reactor at a rate of 2,000 grams/hour. This solution was mixed with an 18 wt. % monochlorobenzene solution (fed into the reactor at a rate of 10 g/h) of tetraethylene glycol (10% excess of OH equivalents). The average dwell time was 40 minutes and the temperature was 130° C. 1,000 g of monochlorobenzene together with 551 g (4.63 M) of phenyl isocyanate and 449 g tetraethylene glycol (4.63 OH equivalents) were pump circulated for 2 hours at 130° C. without the removal of monochlorobenzene by distillation. The mixture of phenyl isocyanate and glycol solutions was then continuously fed into the sump of a distillation column.

As introduction of the monochlorobenzene solutions into the sump was begun, a quantity of distillate corresponding to the quantity of chlorobenzene solution introduced into the reactor was removed from the head of the column at slightly elevated sump temperature without reflux.

The phenyl isocyanate content in the chlorobenzene solution under these conditions (operating time 10 hours) was from 25 to 30 ppm.

Example 5

Example 4 was repeated using the same apparatus, the same conditions and the same quantity of monochlorobenzene (2,000 g/h) having a phenyl isocyanate content of 500 ppm except that the isocyanate solution was distilled in the sump of the column without the addition of tetraethylene glycol and without previous introduction of phenyl isocyanate. The phenyl isocyanate content of the distillate which was about 300 ppm had a tendency to increase in the course of the experiment (operating time 5 hours).

Example 6

(6a) A 15 wt. % solution of a polyamine mixture of the diphenyl methane series containing 90 wt. % diaminodiphenyl methane isomers was fed into a reactor at a rate of 11.88 kg/hr. This solution was phosgenated in known manner by reaction with a 45 wt. % phosgene solution (fed into the reactor at a rate of 9.5 kg/hr) in a continuously operating experimental phosgenation apparatus. The solvent used was chlorobenzene.

(6b) Hydrogen chloride and dissolved excess phosgene were subsequently removed by blowing them out with nitrogen from the reaction mixture obtained in (6a).

(6c) Chlorobenzene (15.3 kg/hr) was subsequently distilled in several stages at atmospheric pressure from the solution obtained in (6b) until a sump temperature of 180° C. was obtained in the last stage. The crude polyisocyanate obtained as distillation residue (2.25 kg/hr) was discharged continuously.

(6d) The chlorobenzene (15.3 kg/hr) obtained by condensation of the chlorobenzene vapors from (6c)

contained 700 ppm of isocyanate groups (calculated as NCO with molecular weight 42) in the form of readily volatile compounds containing isocyanate groups.

(6e) The condensate obtained in (6d) was then reacted under reflux with 150 g/h of a 20 wt. % solution of tetraethylene glycol in chlorobenzene in a stirrer reactor consisting of three 5-liter vessels arranged in a series. After passing through this series of vessels, the reaction mixture was transferred to the sump of a distillation column where pure chlorobenzene having an isocyanate content of less than 10 ppm was distilled off at the top. A chlorobenzene solution containing about 45 wt. % tetraethylene glycol or of urethanes of this glycol and the isocyanate compounds of the condensate was discharged from the sump of the column at the rate of 120 to 150 g/h. The pure chlorobenzene obtained as distillate was subdivided into two partial streams and reused for the preparation of the above-mentioned polyamine solution and phosgene solution.

Example 7

Example 6 was repeated except that in step (d) the chlorobenzene (total 15.3 kg/hr) obtained by condensation of the vapors formed in (c) (which chlorobenzene in this example contained 1050 ppm of isocyanate groups in the form of compounds containing isocyanate groups) was subdivided into two partial streams of 10.1 kg/hr and 5.2 kg/hr, respectively. The second partial stream (5.2 kg/hr) was used for the preparation of fresh phosgene solutions (ii) without removal of the isocyanate group-containing compounds present therein. The first partial stream (10.1 kg/hr) was introduced into the reactor described in Example 6 and was reacted with 150 g/h of a 20 wt. % solution of tetraethylene glycol in chlorobenzene as described in Example 6. After passing through the series of vessels, the resulting reaction mixture was separated in a distillation column into pure chlorobenzene having an isocyanate content of less than 10 ppm and a sump containing excess tetraethylene glycol and urethane. The pure chlorobenzene obtained as distillate was reused for the preparation of fresh amine solution.

In this example, the crude polyisocyanate was also obtained as sump product of stage (c), in a quantity of 2.25 kg/hr, and was continuously discharged.

Example 8

Example 7 was repeated with the exception that the first partial stream obtained in (d) (10.1 kg/hr) which contained about 1050 ppm of isocyanate groups in the form of impurities was reacted under reflux in the reactor with 100 g/h of a 16 wt. % solution of hexamethylene diamine and chlorobenzene. After passage through the series of vessels, the free isocyanate group content was reduced to less than 10 ppm. The thus-treated partial stream was then mixed without further distillation with starting amine (1.78 kg/hr) in an amount such that an approximately 15 wt. % amine solution was formed which solution was again subjected to the phosgenation reaction. The urea derivatives formed by the reaction of hexamethylene diamine with the compounds containing isocyanate groups were discharged together with the end products of the process. These urea derivatives could, if desired, be separated from the end products by distillation.

Example 9

Example 7 was repeated with the exception that the first partial stream (10.1 kg/hr) of chlorobenzene containing compounds carrying isocyanate groups was continuously reacted (without any further treatment) with 1.78 kg/hr of starting amine to produce an approximately 15 wt. % amine solution. After passing through the series of vessels functioning as a mixer, the free isocyanate group content of the reaction mixture was reduced to less than 20 ppm. The amine solution obtained was taken directly to the phosgenation reaction.

What is claimed is:

1. A process for the production of a polyisocyanate comprising:
   (a) reacting a polyamine solution with a solution of phosgene;
   (b) removing excess phosgene and any hydrogen chloride formed during the reaction of (a);
   (c) removing the solvent and volatile isocyanate group-containing compounds from the reaction mixture of (b) by distillation;
   (d) condensing the solvent and volatile compounds removed in (c);
   (e) treating all or a portion of the condensate of (d) with a compound containing isocyanate reactive hydrogen atoms; and optionally,
   (f) removing nonvolatile reaction products formed during the treatment (e); and
   (g) recycling the treatment condensate of (e) or (f) to the reaction mixture.

2. The process of claim 1 wherein the condensate formed in (d) is separated into one portion which may be used in the preparation of the amine solution and another portion useful in the preparation of the phosgene solution.

3. The process of claim 2 wherein the portion which may be used in the preparation of the amine solution is treated with a compound containing isocyanate reactive hydrogen atoms and then recycled without removing nonvolatile reaction products forming during the treatment.

4. The process of claim 1 wherein the solvent is chlorobenzene or o-dichlorobenzene.

5. The process of claim 1 wherein the compound containing isocyanate reactive hydrogen atoms is selected from the group consisting of alcohols, primary and secondary amines and mixtures thereof which compound does not form an azeotropic mixture with the solvent and has a boiling point which is higher than that of the solvent.

6. The process of claim 1 wherein the compound containing isocyanate reactive hydrogen atoms is a primary or secondary monofunctional or polyfunctional amine.

7. The process of claim 1 wherein the compound containing isocyanate reactive hydrogen atoms is the same polyamine used in the polyamine solution of (a).

* * * * *